(12) United States Patent
Scifert

(10) Patent No.: US 11,723,704 B2
(45) Date of Patent: Aug. 15, 2023

(54) BONE STENT AND PORT

(71) Applicant: Warsaw Orthopedic, Inc., Warsaw, IN (US)

(72) Inventor: Jeffrey L. Scifert, Arlington, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 16 days.

(21) Appl. No.: 17/411,175

(22) Filed: Aug. 25, 2021

(65) Prior Publication Data

US 2021/0378725 A1 Dec. 9, 2021

Related U.S. Application Data

(62) Division of application No. 16/273,960, filed on Feb. 12, 2019, now Pat. No. 11,129,658.

(51) Int. Cl.
*A61F 2/44* (2006.01)
*A61B 17/56* (2006.01)
(Continued)

(52) U.S. Cl.
CPC ........ *A61B 17/8808* (2013.01); *A61F 2/4455* (2013.01); *A61F 2/4601* (2013.01);
(Continued)

(58) Field of Classification Search
CPC ............ A61B 17/7061; A61B 17/8808; A61B 17/3462; A61B 17/3423; A61B 2017/564; A61B 2017/3419; A61B 2017/3492; A61F 2/2418; A61F 2/2475; A61F 2/2846; A61F 2/442; A61F 2/4455; A61F 2/4601; A61F 2/4611; A61F 2/2486; A61F 2/1846;
(Continued)

(56) References Cited

U.S. PATENT DOCUMENTS 4,961,740 A * 10/1990 Ray .................. A61F 2/4611
606/279
5,653,718 A 8/1997 Yoon
(Continued)

FOREIGN PATENT DOCUMENTS

EP 2351539 A2 8/2011
WO 2006007090 A2 1/2006

OTHER PUBLICATIONS

Daisuke, et al., Stem cell therapy for intervertebral disc regeneration: obstacles and solutions, <https://www.nature.com/articles/nrrheum.2015.13>, Nature Reviews Rheumatology, vol. 11, pp. 243-256, Feb. 24, 2015.
International Search Report, PCT/US2019/056637 dated Feb. 6, 2020.

*Primary Examiner* — Marcela I. Shirsat
(74) *Attorney, Agent, or Firm* — Fox Rothschild LLP; P. Marshall Ticer

(57) ABSTRACT

A device is disclosed that includes a bone stent positioned within a bony access channel formed within a vertebra. The bony access channel may extends from an outer end of the vertebra through an endplate. The device includes an end cap attached to a proximal end portion of the bone stent and is configured to, post-operatively, open to allow a reintroduction of a material to a spinal intradiscal space or intervertebral disc and to seal access to the spinal intradiscal space or the intervertebral disc after the reintroduction of the material.

20 Claims, 6 Drawing Sheets

(51) Int. Cl.
*A61F 2/24* (2006.01)
*A61B 17/34* (2006.01)
*A61B 17/88* (2006.01)
*A61F 2/46* (2006.01)
*A61F 2/28* (2006.01)
*A61B 17/16* (2006.01)
*A61F 2/30* (2006.01)

(52) U.S. Cl.
CPC .......... *A61F 2/4611* (2013.01); *A61B 17/1671* (2013.01); *A61B 17/3462* (2013.01); *A61B 2017/3419* (2013.01); *A61B 2017/564* (2013.01); *A61F 2/2418* (2013.01); *A61F 2/2475* (2013.01); *A61F 2002/285* (2013.01); *A61F 2002/2817* (2013.01); *A61F 2002/3085* (2013.01); *A61F 2002/30579* (2013.01); *A61F 2002/30845* (2013.01); *A61F 2250/0069* (2013.01); *Y10S 623/90* (2013.01)

(58) Field of Classification Search
CPC .................. A61F 2/24; A61F 2002/285; A61F 2002/30579; A61F 2002/30846; A61F 2002/3085; A61F 2250/0069; Y10S 623/90
USPC ................................ 600/201–235; 623/17.11
See application file for complete search history.

(56) References Cited

U.S. PATENT DOCUMENTS

| 5,683,378 | A | * | 11/1997 | Christy .............. A61B 17/3423 606/1 |
| 6,048,343 | A | | 4/2000 | Mathis et al. |
| 6,730,095 | B2 | | 5/2004 | Olson, Jr. et al. |
| 6,852,095 | B1 | | 2/2005 | Ray |
| 7,575,572 | B2 | | 8/2009 | Sweeney |
| 7,762,998 | B2 | * | 7/2010 | Birk ..................... A61B 17/064 604/288.01 |
| 7,850,704 | B2 | | 12/2010 | Burnett et al. |
| 8,409,133 | B2 | | 4/2013 | Pesach et al. |
| 8,622,991 | B2 | | 1/2014 | Pesach et al. |
| 8,740,954 | B2 | | 6/2014 | Ghobrial et al. |
| 8,827,986 | B2 | | 9/2014 | Shachar et al. |
| 9,445,853 | B2 | | 9/2016 | Crawford et al. |
| 2005/0267555 | A1 | | 12/2005 | Marnfeldt et al. |
| 2006/0195180 | A1 | | 8/2006 | Kheradvar et al. |
| 2009/0138043 | A1 | | 5/2009 | Kohm |
| 2010/0222750 | A1 | | 9/2010 | Cheng |
| 2011/0105848 | A1 | | 5/2011 | Sadovsky et al. |
| 2014/0336710 | A1 | | 11/2014 | Georgy |
| 2015/0057662 | A1 | | 2/2015 | Halanski et al. |
| 2015/0314118 | A1 | | 11/2015 | Kelekis et al. |

* cited by examiner

BONE STENT AND PORT

CROSS-REFERENCE TO RELATED U.S. PATENT APPLICATIONS

This Application is a Divisional Application of U.S. Non-provisional patent application Ser. No. 16/273,960, entitled "BONE STENT AND PORT", filed Feb. 12, 2019, which is incorporated herein by reference in its entirety.

BACKGROUND

Delivery of regenerative medicine or fusion materials to a spinal intradiscal space present a variety of challenges. For instance, it is difficult to deliver regenerative medicine or fusion materials to an intervertebral disc through the annulus fibrosus of the disc without further risking injury to the disc. By puncturing the closed annulus, the disc becomes damaged, which may accelerate disc degeneration. Therefore, it may be challenging to introduce materials to the intradiscal nucleus space without also introducing the potential to further damage the intervertebral disc. Alternatively, in order to access the intervertebral disc and not disrupt the annulus, the regenerative medicine or fusion materials may be delivered via an alternative path that extends through a portion of the bony vertebral anatomy and an endplate exiting into the intradiscal space. However, after the path is generated, the path may heal, thereby closing the path and preventing future therapy deliveries through the same path.

There is a need to provide improved methods and devices that allow for the reintroduction of regenerative medicine or fusion materials into the intradiscal space post-operatively.

SUMMARY

The present disclosure relates generally to devices and methods for treating damaged and/or diseased discs and/or bones. In particular, the present disclosure relates to devices and methods for delivering regenerative medicine and/or fusion materials to the spinal intradiscal space and for reintroducing the medicine and/or fusion materials at a subsequent time.

In one or more embodiments, the disclosed technology relates to a device that includes a bone stent positioned within a bony access channel formed within a vertebra. In one or more embodiments, the bony access channel may extends from an outer end of the vertebra through an endplate. In one or more embodiments, the device includes an end cap attached to a proximal end portion of the bone stent and is configured to, post-operatively, open to allow a reintroduction of a material to a spinal intradiscal space or intervertebral disc and to seal access to the spinal intradiscal space or the intervertebral disc after the reintroduction of the material.

In one or more embodiments, the disclosed technology relates to a method that includes forming a bony access channel within a vertebra that extends from an outer end of the vertebra through an endplate; attaching an end cap to a proximal end portion of a bone stent; and positioning the bone stent within the bony access channel. In one or more embodiments, the end cap is configured to, post-operatively, open allowing a reintroduction of a material to a spinal intradiscal space or intervertebral disc and to seal access to the spinal intradiscal space or intervertebral disc after the reintroduction of the material.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

BRIEF DESCRIPTION OF THE DRAWINGS

The following drawings are illustrative of particular embodiments of the present disclosure and therefore do not limit the scope of the present disclosure. The drawings are not to scale and are intended for use in conjunction with the explanations in the following detailed description.

DETAILED DESCRIPTION

Figure 1B:
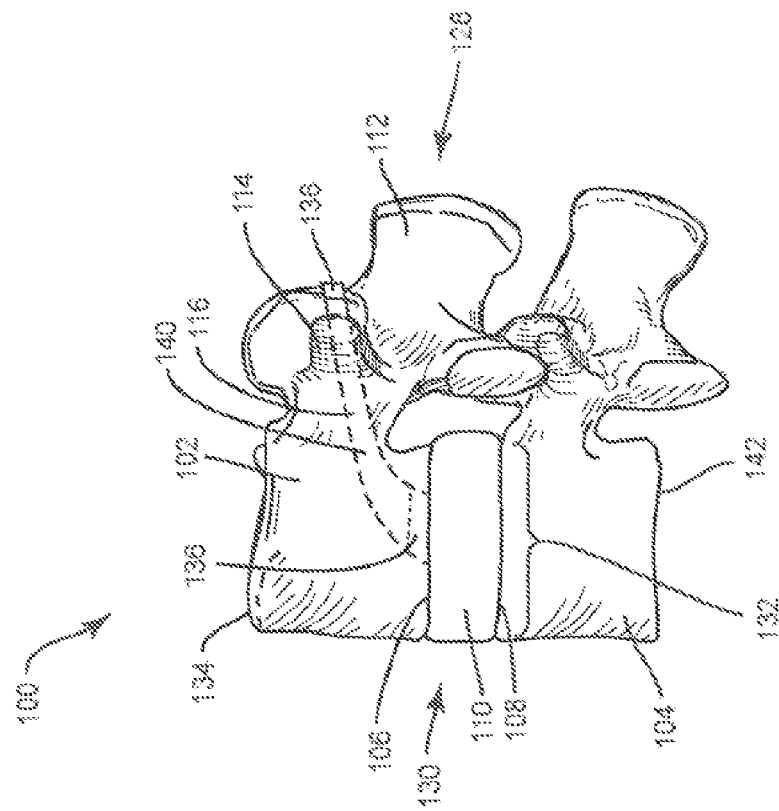
FIG. 1B is a lateral view of a section of vertebrae depicting the bone stent inserted into one of the vertebral bodies, according to one or more embodiments of the present disclosure.

The following discussion omits or only briefly describes conventional features related to treating damaged and/or diseased discs and/or bones which are apparent to those skilled in the art. It is noted that various embodiments are described in detail with reference to the drawings, in which like reference numerals represent like parts and assemblies throughout the several views. Reference to various embodiments does not limit the scope of the claims attached hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally to devices and methods for treating damaged and/or diseased discs and/or bones. In particular, embodiments of the present disclosure relate to devices and methods for delivering regenerative medicine and/or fusion materials to the spinal intradiscal space and for reintroducing the medicine and/or fusion materials at a subsequent time. It should be noted that the term "material" hereinafter may refer to regenerative medicine or fusion materials. Embodiments of the devices and methods are described below with reference to FIGS. 1A-7B.

Figure 1A:
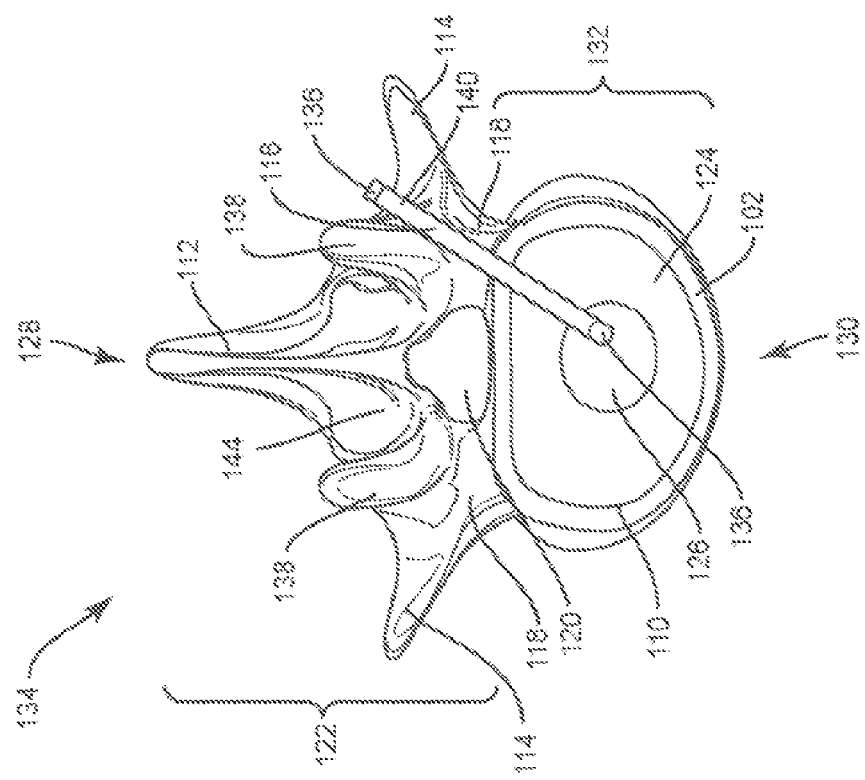
FIG. 1A is a coronal view of a vertebra depicting a bone stent inserted into the vertebral body, according to one or more embodiments of the present disclosure.

FIG. 1A is a coronal view of a vertebra 134 depicting a bone stent 116 inserted into the vertebral body 102, according to one or more embodiments of the present disclosure. FIG. 1B is a lateral view of a section of vertebrae 100 depicting the bone stent 116 inserted into the vertebral body 102, according to one or more embodiments of the present disclosure. It is noted that bone stent 116 can also be a cannula or a lumen. In one or more embodiments, the bone stent 116 may be configured for minimally invasive introduction of disc therapies. Moreover, the bone stent 116 is configured to provide a pathway to re-infuse the intervertebral disc 110 with regenerative therapies or bone graft, and to allow temporal spacing in therapy delivery.

The vertebra 134 includes a vertebral body 102, which is located on the anterior side 130 of the vertebra 134. The vertebral body 102 includes an endplate 106 located on the upper and lower horizontal surfaces of the vertebral body 102. Similarly, the vertebral body 104 includes an endplate 108 located on the upper and lower horizontal surfaces of the vertebral body 104.

The vertebra 134 includes a posterior vertebral arch 122 located on the posterior side 128 of the vertebra 134. The posterior vertebral arch 122 includes a spinous process 112, a lamina 144, left and right superior articular processes 138, left and right transverse processes 114, and left and right pedicles 118. The lamina 144 extends from an end of the spinal canal 120 to the spinous process 112. The left and right pedicles 118 are connected to the vertebral body 102 and extend outwards away from the vertebral body 102. The right and left superior articular processes 138 are located between the lamina 144 and the respective right and left pedicles 118. The posterior vertebral arch 122 and the vertebral body 102 form the spinal canal 120, in which the spinal cord passes through.

An intervertebral disc 110 is located within the intradiscal space 132 between two adjacent vertebral bodies, such as vertebral body 102 and vertebral body 104. The intradiscal space 132 is a region between the two adjacent vertebral bodies in the vertebral column. The intervertebral disc 110 connects the two adjacent vertebral bodies and allows movement of the section of vertebrae 100. The intervertebral disc 110 is composed of an annulus fibrosus 124 and the nucleus pulposus 126. The annulus 124 surrounds the nucleus 126 and is connected to the vertebral endplates 106 and 108.

In one or more embodiments, the bone stent 116 can be placed within a bony access channel 140 to provide a path through the endplate 106 and into the intradiscal space 132 and/or intervertebral disc 110. In one or more embodiments, the bony access channel 140 extends through the right or left pedicle 118 and into a portion of the vertebral body 102. In one or more embodiments, the bony access channel 140 extends through a portion of a right or left transverse process 114, a portion of the adjacent right of left pedicle 118, and into a portion of the vertebral body 102. In one or more embodiments, the bony access channel 140 extends through a portion of the lamina 144, a portion of the right or left pedicle 118, and into a portion of the vertebral body 102. In one or more embodiments, the bony access channel 140 extends through a portion of the right or left superior articular process 138, a portion of the adjacent right of left pedicle 118, and into a portion of the vertebral body 102. In one or more embodiments, the bony access channel 140 extends from a portion the lamina 144, a portion of the right or left superior articular process 138, a portion of the adjacent right of left pedicle 118, and into a portion of the vertebral body 102. In one or more embodiments, the bony access channel 140 extends from the inferior vertebral body 104 through the lower endplate 108 of the disc 110. In one or more embodiments, the bony access channel 140 extends through the anterior or lateral vertebral body. The bone stent 116 may be positioned within any of the aforementioned paths of the bony access channel 140. In one or more embodiments, a longitudinal length of the bone stent 116 may be long enough to extend through the right or left pedicle 118 and into a portion of the vertebral body 102. In one or more embodiments, a longitudinal length of the bone stent 116 may be long enough to extend through a portion of the right or left transverse process 114, a portion of the adjacent right of left pedicle 118, and into a portion of the vertebral body 102. In one or more embodiments, a longitudinal length of the bone stent 116 may be long enough to extend through a portion of the lamina 144, a portion of the right or left pedicle 118, and into a portion of the vertebral body 102. In one or more embodiments, a longitudinal length of the bone stent 116 may be long enough to extend through a portion of the right or left superior articular process 138, a portion of the adjacent right of left pedicle 118, and into a portion of the vertebral body 102. In one or more embodiments, a longitudinal length of the bone stent 116 may be long enough to extend from a portion the lamina 144, a portion of the right or left superior articular process 138, a portion of the adjacent right of left pedicle 118, and into a portion of the vertebral body 102.

In one or more embodiments, the bony access channel 140 may be formed to avoid the annulus fibrosis 124. In one or more embodiments, the bony access channel 140 creates an opening through the endplate 106 of the vertebral body 102. It is noted that the bony access channel 140 can be formed in the vertebra 142 to create an opening through the endplate 108 of the vertebral body 104. The bony access channel 140 formed in the vertebra 142 can follow a similar path as discussed above with respect to the bony access channel 140 formed in the vertebra 134. It is understood that the features discussed with respect to the vertebral body 102 are equally applicable to the vertebral body 104 and other vertebrae that form the spinal column.

Figure 2:
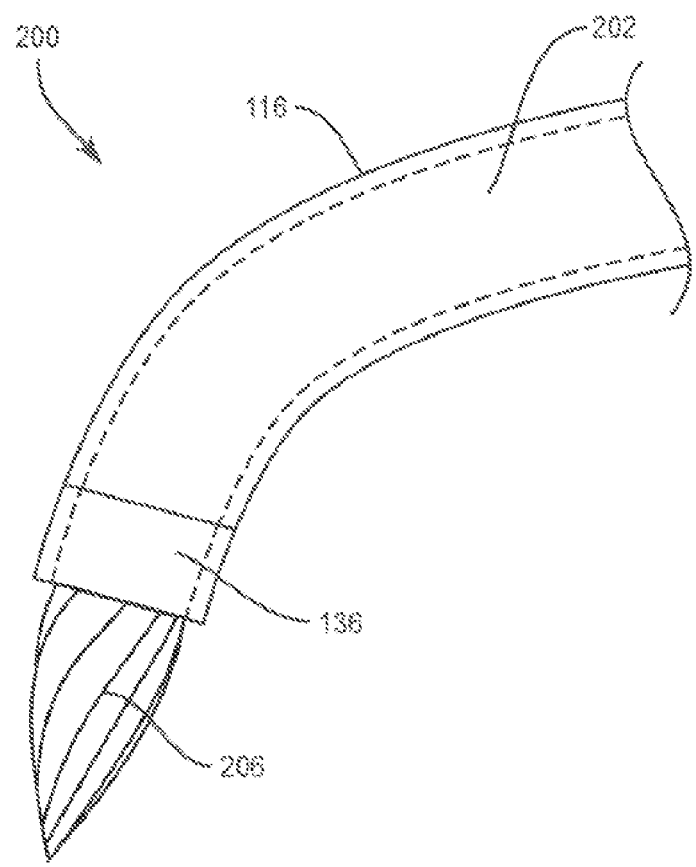
FIG. 2 illustrates a configuration of bone stent and a drill bit and shaft inserted therethrough, according to one or more embodiments of the present disclosure.

FIG. 2 illustrates a configuration 200 of the bone stent 116 and a drill bit 206 and shaft 202 inserted therethrough, according to one or more embodiments of the present disclosure. In one or more embodiments, the bone stent 116 may be configured to allow the drill bit 206 and the shaft 202 to pass through the bone stent 116 exiting an end of the bone stent 116. The drill bit 206 may be connected to a drill, via the shaft 202. The drill bit 206 is configured to drill into bone to create the bony access channel 140. In one or more embodiments, the shaft 202 is linear and forms a linear bony access channel when the drill rotates the drill bit 206 through the vertebra 134. In one or more other embodiments, the shaft 202 may be flexible and/or curved and forms a curved bony access channel when the drill rotates the drill bit 206 through the vertebra 134. Having drilled the bony access channel 140, the drill bit 206 may collapse to a size to fit within the inner diameter of the bone stent 116. The collapsed drill bit 206 is withdrawn from the bone stent 116. In one or more cases, the collapsed drill bit 206 is withdrawn from the bone stent 116 after placement of an endcap 136.

In one or more embodiments, the drill bit 206 may be collapsible, such that the drill bit 206 collapses to a size to fit within the bone stent 116 and expands when the drill bit 206 exits an end of the bone stent 116. The drill bit 206 may be configured to commence drilling when the drill bit 206 may be in the expanded position. To either remove the drill bit 206 from the bone stent 116 or position the drill bit 206 for drilling into the vertebra 134, the drill bit 206 may be configured to pass through the bone stent 116 in the collapsed position. The outer diameter of the drill bit 206 may be equal to the outer diameter of the bone stent 116, in which the outer diameter of the bone stent 116 fits within the bony access channel 140. In one or more other embodiments, the outermost diameter of the drill bit 206 may be about 1%-2% greater than the diameter of the bone stent 116. Having drilled the bony access channel 140, the drill bit 206 collapses to a size to fit within the inner diameter of the bone stent 116. The collapsed drill bit 206 is withdrawn from the bone stent 116. In one or more cases, the collapsed drill bit 206 is withdrawn from the bone stent 116 after placement of an endcap 136.

In one or more embodiments, the end cap 136 may be pre-attached to an end of the bone stent 116. In some embodiments, the end cap 136 may be pre-attached before the drill bit 206 is inserted into the bone stent 116. In one or more embodiments, the end cap 136 may be deployed after the drill bit 206 creates the bony access channel. In one or more embodiments, the end cap 136 may be positioned within at least a portion of the intradiscal space 132, at least a portion of the endplate 106, and/or at least a portion of the vertebral body 102. The end cap 136 may be positioned adjacent to the intradiscal space 132.

In one or more embodiments, the end cap 136 may be attached to a proximal end of the bone stent 116, such that a proximal surface of the end cap 136 and a proximal surface of the bone stent 116 are adjacent to one another. In some embodiments, the outer diameter of the end cap 136 and the outer diameter of the bone stent 116 are equal in size. In other embodiments, the outer diameter of the end cap 136 is no larger than the outer diameter of the bone stent 116 in order for the end cap 136 to fit within the bone stent 116 and be placed within a portion of the bone stent 116. In some other embodiments, the inner diameter of the bone stent 116 is about 1%-2% greater than the outer diameter of the end cap 136 in order for the end cap 136 to fit within the bone stent 116 and be placed within a portion of the bone stent 116. In one or more other embodiments, the end cap 136 is attached within at least a portion of the bone stent 116, in which the outer diameter of the end cap 136 is about 1%-2% less than the inner diameter of the bone stent 116.

In one or more embodiments, the end cap 136 is attached to the bone stent 116, via an adhesive, bonding method, and/or molding method known to one or ordinary skill in the art. In one or more other embodiments, the end cap 136 is attached within the bone stent 116, via the end cap 136 being press fit within the bone stent 116, a compression ring holding the end cap 136 within the bone stent 116, and/or silicon or another flexible sleeve holding the end cap 136 within the bone stent 116. In yet one or more other embodiments, the end cap 136 and bone stent 116 are molded together to form a unitary body.

In one or more embodiments, the drill bit 206 can be configured to create the bony access channel 140 without being inserted through the bone stent 116. That is, the bony access channel 140 can be created via the drill bit 206, and after which, the bone stent 116 is inserted into the bony access channel 140. In one or more embodiments, after the bone stent 116 is inserted into the bony access channel 140, the end cap 136 is inserted into the bone stent 116 and is positioned within a portion of the intradiscal space 132, a portion of the endplate 106, and/or a portion of the vertebral body 102. The end cap may further be attached to the drill used to create the bony insertion access.

Figure 3A:
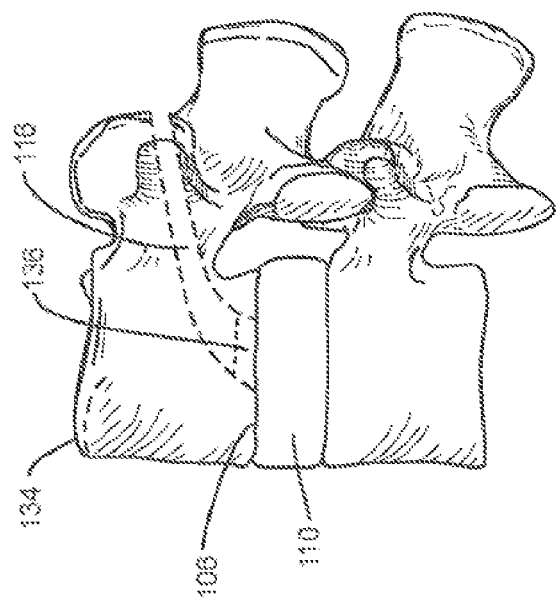
FIGS. 3A-3B illustrate the insertion of the bone stent and one or more end caps into a vertebra, according to one or more embodiments of the present disclosure.
Figure 3B:
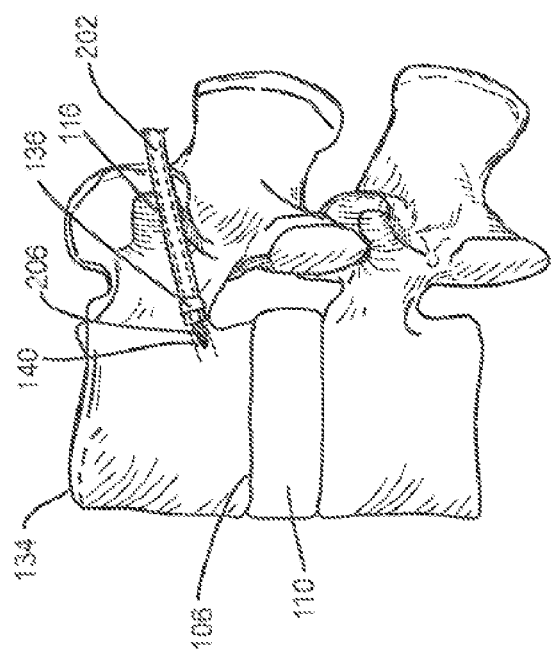

FIGS. 3A-3B illustrate the insertion of the bone stent 116 and one or more end caps 136 into the vertebra 134, according to one or more embodiments of the present disclosure.

In one or more embodiments, a user, utilizing the bone stent configuration 200, drills into a portion of the vertebra 134 to create the bony access channel 140, in order to provide a pathway through the endplate 106 and into the intradiscal space 132 and/or intervertebral disc 110. Having drilled the bony access channel 140, the user collapses and removes the drill bit 206 from the bone stent 116.

For the cases in which the end cap 136 is pre-attached to the bone stent 116, in one or more embodiments, the user inserts a separate attachment mechanism into the bone stent 116 to anchor the end cap 136, in a manner described with respect to end cap 136a and 136b, into at least a portion of the endplate 106 and/or a portion of the vertebral body 102. In one or more other embodiments, the end cap 136 self-anchors, in a manner described with respect to end cap 136a, into at least a portion of the endplate 106 and/or a portion of the vertebral body 102.

Figure 7B:
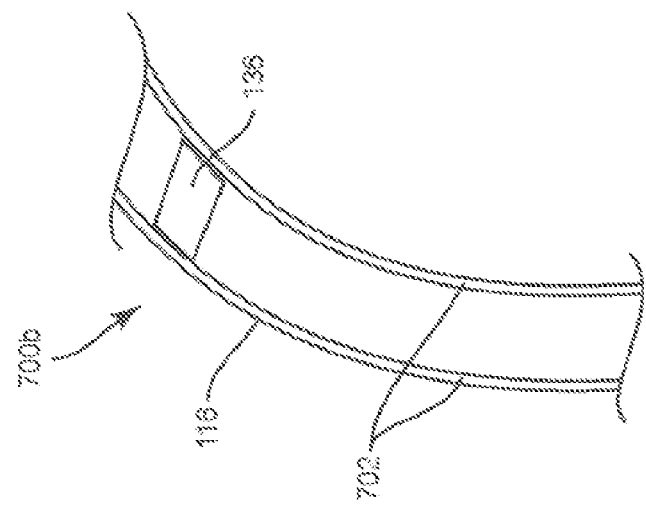
FIG. 7B illustrates an interior view of the bone stent, according to one or more embodiments of the present disclosure.
Figure 7A:
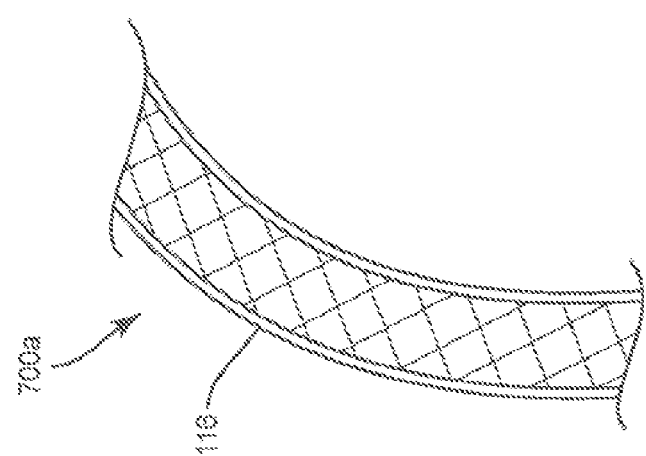
FIG. 7A illustrates an exterior view of the bone stent, according to one or more embodiments of the present disclosure.

For the cases in which the end cap 136 is inserted into the bone stent 116 after the bone stent 116 is positioned within the bony access channel 140, the user may position the end cap 136 into at least a portion of the endplate 106 and/or a portion of the vertebral body 102, using one or more guide channels 702 or other alignment mechanisms as further describe in the description of FIGS. 7A and 7B. After positioning the end cap 136, the user inserts a separate attachment mechanism into the bone stent 116 to anchor the end cap 136 into at least a portion of the endplate 106 and/or a portion of the vertebral body 102.

In one or more embodiments, once the end cap 136 is positioned, the end cap 136 and bone stent 116 remain in place, allowing for the delivery of one or more materials to the intradiscal space 132. The one or more materials may pass through the inner portion of the bone stent 116, and may enter the disc nuclear space through the end cap 136. Having the end cap 136 and bone stent 116 remain in place allows for the reintroduction of the one or more materials at a subsequent time, such as post-operatively. For instance, a given therapy (e.g., cell therapy, drug therapy, biologics, or a combination of the aforementioned) can be introduced at select times throughout the therapy, and repeat injections of the therapy can be administered through the bone stent 116. Moreover, another end cap, i.e., a distal end cap, may be positioned at an opposite end of the bone stent 116 to seal the inner portion of the bone stent 116. By sealing the inner portion of the bone stent 116, the other end cap may prevent bone and tissue from infiltrating the inner portion of the bone stent 116 and closing off access to the end cap 136, thereby keeping the inner portion of the bone stent 116 open and allowing for reintroduction of medicine and/or fusion materials at a subsequent time. The distal end cap may include one or more of the features described with respect to the end cap 136, i.e., the proximal end cap. In one or more embodiments, the distal end cap may be anchored to a portion of the vertebral body 102; an outer end portion of a left or right pedicle 118; an outer end portion of a left or right transverse process 114; an outer end portion of a left or right pedicle 118 and an adjacent left or right transverse process 114; an outer end portion of the lamina 144; or an outer end portion of the left or right superior articular process 138.

Figure 4C:
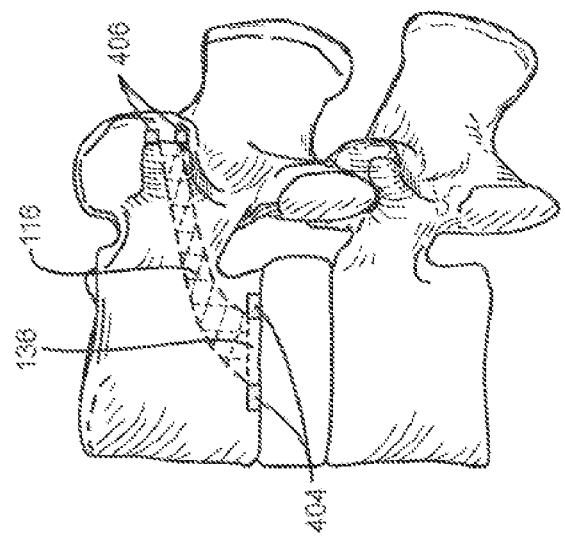
FIGS. 4A-4C illustrate the insertion of the bone stent, using a docking ring, into a vertebra, according to one or more embodiments of the present disclosure.
Figure 4B:
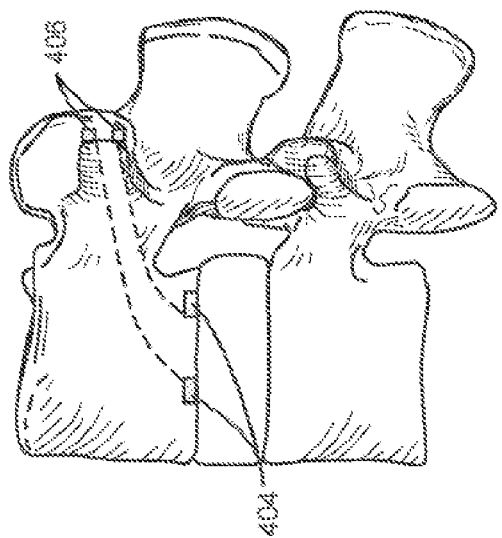
Figure 4A:
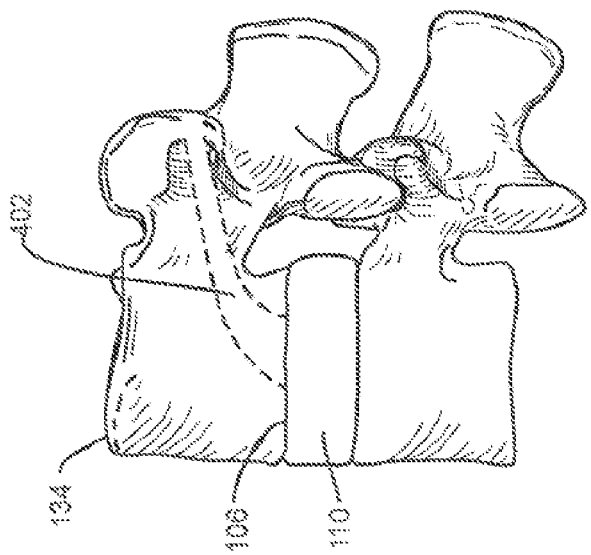

FIGS. 4A-4C illustrate the insertion of the bone stent 116, using a docking ring 402, into the vertebra 134, according to one or more embodiments of the present disclosure.

In one or more embodiments, a user drills a pathway 402, i.e., a bony access channel, using a drill bit similar to that of drill bit 206. The user drills into a portion of the vertebra 134 to create the pathway 402 through the endplate 106 and into the intradiscal space 132 and/or intervertebral disc 110. The drill bit is connected to a drill, via a shaft similar to shaft 202. In one or more embodiments, the user positions a docking ring 404 on a portion of the endplate 106 and/or an end portion of the vertebra 134. The user may deploy the docking ring 404, thereby anchoring the docking ring 404 into a portion of the endplate 106 and/or an end portion of the vertebra 134. In one or more embodiments, the docking ring 404 is anchored via one of deployable spikes similar to the deployable spike configuration 136a; a circumferential bone-cutting thread configuration similar to the circumferential bone-cutting thread end cap configuration 136b; or a deployable anchoring blade configuration similar to the deployable anchoring blade end cap configuration 136c. In one or more embodiments, the pathway 402 is large enough to accommodate the outer diameter of the docking ring 404 as the docking ring 404 is positioned. For the cases in which the docking ring 404 is anchored, the outer diameter of the docking ring 404 may be greater than the diameter of the pathway 402.

Having anchored the docking ring 404, the user can insert the bone stent 116 into the pathway 402. In one or more embodiments, the docking ring 404 may include a threaded portion on an interior surface, in which the threaded portion is configured to receive a threaded portion on an exterior surface of the end cap 136 or the bone stent 116. The user may insert and rotate the end cap 136 and/or bone stent 116 into the interior surface of the docking ring 404, thereby fastening the end cap 136 and/or the bone stent 116 to the docking ring 404. In one or more other embodiments, the end cap 136 and/or bone stent 116 are press fit or snapped into the interior surface of the docking ring 404, thereby fastening the end cap 136 and/or the bone stent 116 to the docking ring 404. In one or more embodiments, a second docking ring 406 is anchored to a portion of the vertebral body 102; an outer end portion of a left or right pedicle 118; an outer end portion of a left or right transverse process 114; an outer end portion of a left or right pedicle 118 and an adjacent left or right transverse process 114; an outer end portion of the lamina 144; or an outer end portion of the left or right superior articular process 138. A distal end cap attached to the bone stent 116 and/or the bone stent 116 may be fastened to the second docking ring 406 in a manner similar to the end cap 136 and/or the bone stent 116 being fastened to the docking ring 404.

Figure 5A:
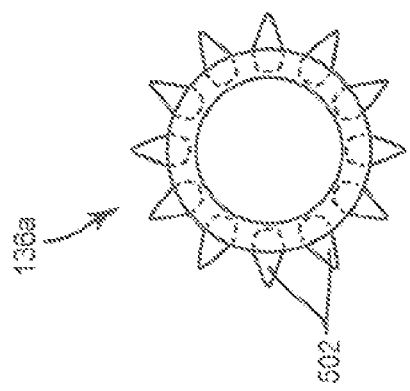
FIGS. 5A-5C illustrate top views of anchoring configurations of the end cap, according to one or more embodiments of the present disclosure.
Figure 5B:
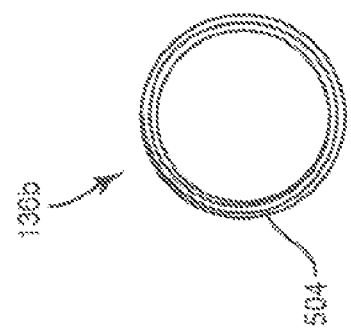
Figure 5C:
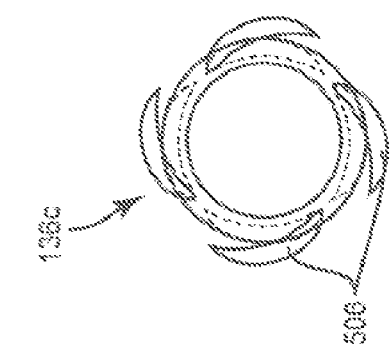

FIGS. 5A-5C illustrate top views of anchoring configurations of the end cap 136, according to one or more embodiments of the present disclosure. In one or more embodiments, the end cap 136 is configured to be anchored into at least a portion of the endplate 106 and/or a portion of the vertebral body 102.

In one or more embodiments, the end cap 136 utilizes a deployable spike end cap configuration 136a. The deployable spike end cap configuration 136a includes one or more spikes 502 circumferentially disposed around the end cap 136a. The spikes 502 are configured to be positioned within the end cap 136a. When the end cap 136a is positioned within at least a portion of the endplate 106 and/or a portion of the vertebral body 102, the spikes 502 are deployed into at least a portion of the endplate 106 and/or a portion of the vertebral body 102, thereby anchoring the end cap 136a. That is, the spikes 502 self-seat into at least a portion of the endplate 106 and/or a portion of the vertebral body 102 as the spikes 502 are deployed. A small deployment tool may be used to deploy the spikes 502. In some cases, the deployment tool may be a part of the tool that deploys the bone stent 116. In other cases, the deployment tool may be a separate tool from the tool that deploys the bone stent 116.

In one or more embodiments, the end cap 136 utilizes a circumferential bone-cutting thread end cap configuration 136b. The end cap configuration 136b includes a bone-cutting thread portion 504, which is circumferentially disposed around at least a portion of the end cap 136b. As the end cap 136b is positioned within at least a portion of the endplate 106 and/or a portion of the vertebral body 102, the bone-cutting thread portion 504 fastens the end cap 136b into at least a portion of the endplate 106 and/or a portion of the vertebral body 102, thereby anchoring the end cap 136b. That is, the bone-cutting thread portion 504 self-seats into at least a portion of the endplate 106 and/or a portion of the vertebral body 102 as the end cap 136b is rotated.

In one or more embodiments, the end cap 136 utilizes a deployable anchoring blade end cap configuration 136c. The deployable anchoring blade configuration 136c includes one or more blades 506 circumferentially disposed around the end cap 136c. The blades 506 are configured to be positioned within the end cap 136c. When the end cap 136c is positioned within at least a portion of the endplate 106 and/or a portion of the vertebral body 102, the blades 506 are deployed into at least a portion of the endplate 106 and/or a portion of the vertebral body 102, thereby anchoring the end cap 136c. That is, the one or more blades 506 self-seat into at least a portion of the endplate 106 and/or a portion of the vertebral body 102 as the one or more blades 506 are deployed.

Figure 6A:
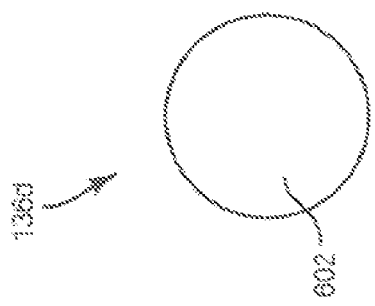
FIGS. 6A-6C illustrate top views of port configurations of the end cap, according to one or more embodiments of the present disclosure.
Figure 6B:
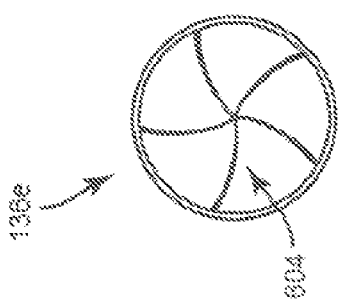
Figure 6C:
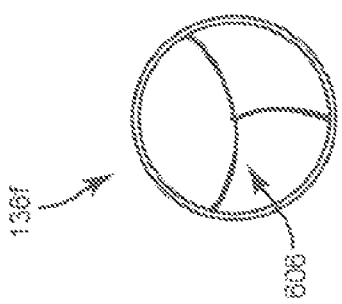

FIGS. 6A-6C illustrate top views of port configurations of the end cap 136, according to one or more embodiments of the present disclosure. In one or more embodiments, the end cap 136 is configured to facilitate the entry of a needle or another delivery mechanism for delivering one or more materials to the spinal intradiscal space 132 and/or the intervertebral disc 110. In one or more embodiments, the end cap 136 is configured to facilitate the entry of a needle or another delivery mechanism for cell therapies, pharmaceuticals, proteins, biologics, or other regenerative medicine products inserted into the intervertebral disc 110. In one or more embodiments, the port configurations of end cap 136d, 136e, and 136f are configured to allow for re-introduction of one or more materials to the spinal intradiscal space 132 and/or the intervertebral disc 110 when the bone stent 116 and endcap 136 are positioned within the vertebra 134 and one or more subsequent times, such as post-operation from positioning the bone stent 116 and end cap 136 within the vertebra 134.

In one or more embodiments, the end cap 136 utilizes a self-sealing port end cap configuration 136d. The end cap 136d is configured to be self-sealing in order to maintain pressurization of the intervertebral disc 110. The port 602 of the end cap 136d may be comprised of rubber, silicon, or another self-sealing material known to one of ordinary skill in the art. In one or more embodiments, the port 602 opens as the drill bit 206, a needle, or another delivery mechanism is inserted through the port 602 to the intradiscal space 132 and/or the intervertebral disc 110. In one or more embodiments, the port 602 self-seals as the drill bit 206, a needle, or another delivery mechanism is removed from the end cap 136d.

In one or more embodiments, the end cap 136 may utilize an iris opening end cap configuration 136e. The iris opening 604 is configured to be manually opened to provide access to the intervertebral disc 110. The iris opening 604 is configured to be manually closed to seal and/or reseal the end cap 136e in order to maintain pressurization of the intervertebral disc 110.

In one or more embodiments, the end cap 136 may utilize a leaflet valve end cap configuration 136f. The leaflet valve 606 may be configured to open under directional pressure or fluid flow towards the intradiscal space 132 and/or the intervertebral disc 110. The leaflet valve 606 may be configured to self-seal when the directional pressure or fluid flow ends or is below a threshold value.

In one or more embodiments, the port configurations of end cap 136d, 136e, and 136f can be combined with the anchoring configurations of end cap 136a, 136b, and 136c, in one or more combinations. For example, the anchoring configuration of end cap 136a may be combined with the port configuration of end cap 136d; the anchoring configuration of end cap 136b may be combined with the port configuration of end cap 136e; and the anchoring configuration of end cap 136c may be combined with the port configuration of end cap 136f.

FIG. 7A illustrates an exterior view 700a of the bone stent 116, according to one or more embodiments of the present disclosure. FIG. 7B illustrates an interior view 700b of the bone stent 116, according to one or more embodiments of the present disclosure.

In one or more embodiments, the bone stent 116 may include an end cap 136 at both the proximal and distal end of the bone stent 116. Two end caps 136 may be included at both ends of the bone stent 116. In one or more embodiments, the bone stent 116 may be comprised of a flexible biocompatible material that is impermeable to cells on the exterior surface of the bone stent 116. In one or more other embodiments, the bone stent 116 is comprised of a flexible biocompatible material that is impermeable to cells on the exterior surface of the bone stent 116; and that covers a stiffer mesh-like endoskeleton material, such as, nitinol or other shape-memory material, cobalt chromium alloy, or stainless steel 316L. In yet one or more other embodiments, the bone stent 116 is comprised of a flexible biocompatible material that is impermeable to cells on the exterior surface of the bone stent 116; that covers a stiffer mesh-like endoskeleton material, such as, nitinol or other shape-memory material, cobalt chromium alloy, or stainless steel 316L; and that contains a coating to prevent cell adhesion. In one or more embodiments, the bone stent 116 may include one or more guide channels 702 or other alignment mechanisms, for the cases in which an endcap 136 is inserted into the bone stent 116 after the bone stent 116 is inserted into the bony access channel 140 or pathway 402. The one or more guide channels 702 or other alignment mechanisms are configured to position the end cap 136 into at least a portion of the endplate 106 and/or a portion of the vertebral body 102. For the cases in which the bone stent 116 is installed by pushing the end cap 136 at the proximal end of the bone stent 116 through the bony access channel, the bone stent 116 may be flexible enough to unfold in an accordion-like fashion as the end cap 136 at the proximal end moves through the bony access channel and/or one or more guide channels.

The various embodiments described above are provided by way of illustration only and should not be construed to limit the claims attached hereto. Those skilled in the art will readily recognize various modifications and changes that may be made without following the example embodiments and applications illustrated and described herein, and without departing from the spirit and scope of the claims.

What is claimed is:

1. A method for installing a bone stent, comprising:
forming an access channel within a bone of a patient;
attaching an end cap to a proximal end portion of a bone stent;
positioning the bone stent within the access channel;
introducing a first material into the bone stent;
maintaining the bone stent within the access channel post-operatively; and
opening, post-operatively, the endcap and introducing a second material into the bone stent.

2. The method of claim 1, wherein the first material and the second material are the same type of material.

3. The method of claim 1, wherein the first material and the second material are each respectively chosen from the group comprising: regenerative medicine materials and fusion materials.

4. The method of claim 1, wherein the first material and the second material are each respectively chosen from the group comprising: cell therapy materials, drug therapy materials, and biologics materials.

5. The method of claim 1, wherein the bone of the patient is a vertebra.

6. The method of claim 5, wherein the access channel extends from an outer end of the vertebra through an endplate of the vertebra.

7. The method of claim 6, wherein the opening the endcap and introducing a second material into the bone stent step further comprises introducing the second material to a spinal intradiscal space or intervertebral disc.

8. The method of claim 7, further comprising: sealing access to the spinal intradiscal space or the intervertebral disc after introducing the second material.

9. The method of claim 5, wherein positioning the bone stent within the access channel further comprises positioning the bone stent through a pedicle of the vertebra and into a portion of the vertebra.

10. The method of claim 5, wherein positioning the bone stent within the access channel further comprises positioning the bone stent through a portion of a transverse process, a portion of an adjacent pedicle, and into a portion of the vertebra.

11. The method of claim 5, wherein positioning the bone stent within the access channel further comprises positioning the bone stent through a portion of a lamina, a portion of a pedicle, and into a portion of the vertebra.

12. The method of claim 5, wherein positioning the bone stent within the access channel further comprises positioning the bone stent through a portion of a superior articular process, a portion of an adjacent pedicle, and into a portion of the vertebra.

13. The method of claim 5, wherein positioning the bone stent within the access channel further comprises positioning the bone stent from a portion of a lamina, a portion of a superior articular process, a portion of an adjacent pedicle, and into a portion of the vertebra.

14. The method of claim 1, further comprising: pre-attaching the endcap to the proximal end portion of the bone stent prior to positioning the bone stent within the access channel.

15. The method of claim 1, further comprising: positioning the end cap into at least one of: a portion of an endplate of a vertebra and a portion of the vertebra.

16. The method of claim 1, further comprising:
attaching an additional end cap to a distal end of the bone stent,
wherein the additional end cap forms a seal with an inner portion of the bone stent.

17. The method of claim 1, further comprising:
anchoring a docking ring to at least one of a portion of an endplate of a vertebra and a portion of the vertebra; and
attaching the end cap and the bone stent to the anchored docking ring.

18. The method of claim 17, further comprising:
anchoring an additional docking ring to an outer end portion of the vertebra; and
attaching an additional end cap to of the bone stent,
wherein the additional end cap forms a seal with an inner portion of the bone stent, and
wherein the additional end cap and the bone stent are attached to the additional docking ring.

19. The method of claim 1, further comprising:
deploying one or more deployable spikes and/or anchoring blades to seat into at least one of: a portion of an endplate of a vertebra and a portion of a vertebral body,
wherein the one or more deployable spikes are circumferentially disposed around the end cap.

20. The method of claim 1, further comprising:
anchoring a circumferential bone-cutting thread portion within a portion of an endplate of a vertebra and a portion of the vertebra,
wherein the circumferential bone-cutting thread portion is disposed on an outer end of the end cap.

* * * * *